(12) United States Patent
Bedingham et al.

(10) Patent No.: US 7,322,254 B2
(45) Date of Patent: Jan. 29, 2008

(54) VARIABLE VALVE APPARATUS AND METHODS

(75) Inventors: William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/734,717

(22) Filed: Dec. 12, 2003

(65) Prior Publication Data

US 2005/0126312 A1  Jun. 16, 2005

(51) Int. Cl.
*G01N 1/00* (2006.01)
(52) U.S. Cl. ..................... 73/863.86; 422/72
(58) Field of Classification Search ............. 73/863.21, 73/863.31, 863.81, 863.86, 864, 864.34, 73/864.81, 61.48, 61.72; 422/64, 72, 81, 422/82.05, 99; 250/428, 430, 432 R
See application file for complete search history.

(56) References Cited

U.S. PATENT DOCUMENTS

| | | | |
|---|---|---|---|
| 4,839,296 A | 6/1989 | Kennedy et al. | |
| 5,079,155 A | 1/1992 | Cox et al. | |
| 5,182,083 A | 1/1993 | Barker et al. | |
| 5,264,184 A | 11/1993 | Aysta et al. | |
| 5,438,128 A | 8/1995 | Nieuwkerk et al. | |
| 5,464,541 A | 11/1995 | Aysta et al. | |
| 5,691,208 A | 11/1997 | Miltenyi et al. | |
| 5,976,468 A * | 11/1999 | Godec et al. ............... | 422/100 |
| 5,997,818 A | 12/1999 | Hacker et al. | |
| 6,007,690 A | 12/1999 | Nelson et al. | |
| 6,048,457 A | 4/2000 | Kopaciewicz et al. | |
| 6,063,589 A | 5/2000 | Kellogg et al. | |
| 6,068,751 A | 5/2000 | Neukermans et al. | |
| 6,074,827 A | 6/2000 | Nelson et al. | |

(Continued)

FOREIGN PATENT DOCUMENTS

EP   0 281 368 A   9/1988

(Continued)

OTHER PUBLICATIONS

Emmer Asa et al.; "Wall deactivation with fluorosurfactants for capillary electrophoretic analysis of biomolecules" *ELECTROOPHORESIS*, vol. 22, No. 4, Feb. 2001; pp. 660-665, XP002325650; ISSN: 0173-0835, p. 664.

(Continued)

*Primary Examiner*—Robert Raevis
(74) *Attorney, Agent, or Firm*—Kevin W. Raasch

(57) ABSTRACT

Sample processing devices with variable valve structures and methods of using the same are disclosed. The valve structures allow for removal of selected portions of the sample material located within the process chamber. Removal of the selected portions is achieved by forming an opening in a valve septum at a desired location. The valve septums may be large enough to allow for adjustment of the location of the opening based on the characteristics of the sample material in the process chamber. If the sample processing device is rotated after the opening is formed, the selected portion of the material located closer to the axis of rotation exits the process chamber through the opening. The remainder of the sample material cannot exit through the opening because it is located farther from the axis of rotation than the opening.

29 Claims, 3 Drawing Sheets

U.S. PATENT DOCUMENTS

| | | |
|---|---|---|
| 6,103,199 A | 8/2000 | Bjornson et al. |
| 6,143,247 A | 11/2000 | Sheppard, Jr. et al. |
| 6,143,248 A | 11/2000 | Kellogg et al. |
| 6,168,948 B1 | 1/2001 | Anderson et al. |
| 6,197,595 B1 | 3/2001 | Anderson et al. |
| 6,200,474 B1 | 3/2001 | Kopaciewicz et al. |
| 6,265,168 B1 | 7/2001 | Gjerde et al. |
| 6,284,113 B1 | 9/2001 | Bjornson et al. |
| 6,302,134 B1 | 10/2001 | Kellogg et al. |
| 6,306,273 B1 | 10/2001 | Wainright et al. |
| 6,319,469 B1 | 11/2001 | Mian et al. |
| 6,344,326 B1 | 2/2002 | Nelson et al. |
| 6,440,725 B1 | 8/2002 | Pourahmadi et al. |
| 6,450,047 B2 | 9/2002 | Swedberg et al. |
| 6,451,260 B1 | 9/2002 | Düsterhoft et al. |
| 6,465,225 B1 | 10/2002 | Fuhr et al. |
| 6,479,300 B1 | 11/2002 | Jiang et al. |
| 6,527,432 B2 | 3/2003 | Kellogg et al. |
| 6,532,997 B1 | 3/2003 | Bedingham et al. |
| 6,548,788 B2 | 4/2003 | Takahashi |
| 6,582,662 B1 | 6/2003 | Kellogg et al. |
| 6,617,136 B2 | 9/2003 | Parthasarathy et al. |
| 6,627,159 B1 | 9/2003 | Bedingham et al. |
| 6,632,399 B1 | 10/2003 | Kellogg et al. |
| 6,664,104 B2 | 12/2003 | Pourahmadi et al. |
| 6,692,596 B2 | 2/2004 | Moll et al. |
| 6,720,187 B2 | 4/2004 | Bedingham et al. |
| 6,723,236 B2 | 4/2004 | Fisk et al. |
| 6,730,516 B2 | 5/2004 | Jedrzejewski et al. |
| 6,734,401 B2 | 5/2004 | Bedingham et al. |
| 6,780,818 B2 | 8/2004 | Gundel et al. |
| 6,814,935 B2 | 11/2004 | Harms et al. |
| 7,026,168 B2 | 4/2006 | Bedingham et al. |
| 7,192,560 B2 | 3/2007 | Parthasarathy et al. |
| 2001/0045000 A1 | 11/2001 | Gundel et al. |
| 2002/0047003 A1 | 4/2002 | Bedingham et al. |
| 2002/0048533 A1 | 4/2002 | Harms et al. |
| 2002/0064885 A1 | 5/2002 | Bedingham et al. |
| 2003/0013203 A1 | 1/2003 | Jedrzejewski et al. |
| 2003/0017567 A1 | 1/2003 | Parthasarathy et al. |
| 2003/0044322 A1 | 3/2003 | Andersson et al. |
| 2003/0053934 A1 | 3/2003 | Andersson et al. |
| 2003/0120062 A1 | 6/2003 | Parthasarathy et al. |
| 2003/0138779 A1 | 7/2003 | Parthasarathy et al. |
| 2003/0139550 A1 | 7/2003 | Savu et al. |
| 2003/0152491 A1 | 8/2003 | Kellogg et al. |
| 2003/0155034 A1 | 8/2003 | De Beukeleer et al. |
| 2003/0228706 A1 | 12/2003 | Ramstad et al. |
| 2004/0016702 A1 | 1/2004 | Hennessy et al. |
| 2004/0018116 A1 | 1/2004 | Desmond et al. |
| 2004/0209258 A1 | 10/2004 | Parthasarathy et al. |
| 2005/0130177 A1 | 6/2005 | Bedingham et al. |
| 2005/0142563 A1 | 6/2005 | Haddad et al. |
| 2005/0142570 A1 | 6/2005 | Parthasarathy et al. |
| 2005/0142571 A1 | 6/2005 | Parthasarathy et al. |
| 2005/0142663 A1 | 6/2005 | Parthasarathy et al. |
| 2006/0013732 A1 | 1/2006 | Parthasarathy et al. |

FOREIGN PATENT DOCUMENTS

| | | |
|---|---|---|
| WO | WO 95/19781 A | 7/1995 |
| WO | WO 97/21090 A | 6/1997 |
| WO | 98/04909 A1 | 2/1998 |
| WO | 99/15876 A1 | 4/1999 |
| WO | 99/15888 A1 | 4/1999 |
| WO | 99/40174 A1 | 8/1999 |
| WO | 99/46591 A2 | 9/1999 |
| WO | 99/46591 A3 | 9/1999 |
| WO | 00/62051 A2 | 10/2000 |
| WO | 00/62051 A3 | 10/2000 |
| WO | 01/12327 A1 | 2/2001 |
| WO | 01/38865 A1 | 5/2001 |
| WO | WO 01/30995 A | 5/2001 |
| WO | 03/054509 A2 | 7/2003 |
| WO | 03/054509 A3 | 7/2003 |
| WO | 03/054510 A2 | 7/2003 |
| WO | 03/054510 A3 | 7/2003 |
| WO | 03/058224 A1 | 7/2003 |
| WO | 2004/010760 A2 | 2/2004 |
| WO | 2004/011142 A1 | 2/2004 |
| WO | 2004/011681 A1 | 2/2004 |
| WO | 2004/094672 A1 | 11/2004 |
| WO | WO 2005/005045 A | 1/2005 |

OTHER PUBLICATIONS

Garcia et al., "Comparison of Two Leukocyte Extraction Methods for Cytomegalovirus Antigenemia Assay," Journal of Clinical Microbiology, Jan. 1996; 34(1):182-184.

* cited by examiner

VARIABLE VALVE APPARATUS AND METHODS

Sample processing devices including process chambers in which various chemical or biological processes are performed play an increasing role in scientific and/or diagnostic investigations. The process chambers provided in such devices are preferably small in volume to reduce the amount of sample material required to perform the processes.

One persistent issue associated with sample processing devices including process chambers is in the transfer of fluids between different features in the devices. Conventional approaches to separate and transfer fluidic contents of process chambers have often required human intervention (e.g., manual pipetting) and/or robotic manipulation. Such transfer processes suffer from a number of disadvantages including, but not limited to, the potential for errors, complexity and associated high costs, etc.

Attempts to address the fluid transfer issues have focused on transferring the entire fluid contents of the process chambers through, e.g., valves, tortuous paths, etc.

SUMMARY OF THE INVENTION

The present invention provides sample processing devices with valve structures. The valve structures allow for removal of selected portions of the sample material located within the process chamber. Removal of the selected portions is achieved by forming an opening in a valve septum at a desired location.

The valve septums are preferably large enough to allow for adjustment of the location of the opening based on the characteristics of the sample material in the process chamber. If the sample processing device is rotated after the opening is formed, the selected portion of the material located closer to the axis of rotation exits the process chamber through the opening. The remainder of the sample material cannot exit through the opening because it is located farther from the axis of rotation than the opening.

The openings in the valve septum may be formed at locations based on one or more characteristics of the sample material detected within the process chamber. It may be preferred that the process chambers include detection windows that transmit light into and/or out of the process chamber. Detected characteristics of the sample material may include, e.g., the free surface of the sample material (indicative of the volume of sample material in the process chamber). Forming an opening in the valve septum at a selected distance radially outward of the free surface can provide the ability to remove a selected volume of the sample material from the process chamber.

For sample materials that can be separated into various components, e.g., whole blood, rotation of the sample processing device may result in separation of the plasma and red blood cell components, thus allowing for selective removal of the components to, e.g., different process chambers.

In some embodiments, it may be possible to remove selected aliquots of the sample material by forming openings at selected locations in one or more valve septums. The selected aliquot volume can be determined based on the radial distance between the openings (measured relative to the axis of rotation) and the cross-sectional area of the process chamber between the opening.

The openings in the valve septums are preferably formed in the absence of physical contact, e.g., through laser ablation, focused optical heating, etc. As a result, the openings can preferably be formed without piercing the outermost layers of the sample processing device, thus limiting the possibility of leakage of the sample material from the sample processing device.

In one aspect, the present invention provides a valved process chamber on a sample processing device, the valved process chamber including a process chamber having a process chamber volume located between opposing first and second major sides of the sample processing device, wherein the process chamber occupies a process chamber area on the sample processing device, and wherein the process chamber area has a length and a width transverse to the length, and further wherein the length is greater than the width. The valved process chamber also includes a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device. A detection window is located within the process chamber area, wherein the detection window is transmissive to selected electromagnetic energy directed into and/or out of the process chamber volume.

In another aspect, the present invention provides a valved process chamber on a sample processing device, the valved process chamber including a process chamber having a process chamber volume located between opposing first and second major sides of the sample processing device, wherein the process chamber occupies a process chamber area on the sample processing device, and wherein the process chamber area has a length and a width transverse to the length, and further wherein the length is greater than the width. The valved process chamber also includes a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device, and further wherein the valve chamber and the detection window occupy mutually exclusive portions of the process chamber area, and still further wherein at least a portion of the valve chamber is located within a valve lip extending into the process chamber area, and wherein the valve septum is formed in the valve lip. A detection window is located within the process chamber area, wherein the detection window is transmissive to selected electromagnetic energy directed into and/or out of the process chamber volume.

In another aspect, the present invention comprises a method of selectively removing sample material from a process chamber. The method includes providing a sample processing device that includes a process chamber having a process chamber volume, wherein the process chamber occupies a process chamber area on the sample processing device; a valve chamber located within the process chamber area, wherein the valve chamber is isolated from the process chamber by a valve septum located between the valve chamber and the process chamber; and a detection window located within the process chamber area, wherein the detection window is transmissive for selected electromagnetic energy. The method further includes providing sample material in the process chamber; detecting a characteristic of the sample material in the process chamber through the detection window; and forming an opening in the valve septum at a selected location along the length of the process chamber, wherein the selected location is correlated to the detected characteristic of the sample material. The method also includes moving only a portion of the sample material from the process chamber into the valve chamber through the opening formed in the valve septum.

In another aspect, the present invention provides a method of selectively removing sample material from a process chamber. The method includes providing a sample processing device having a process chamber with a process chamber volume, wherein the process chamber occupies a process chamber area on the sample processing device, and wherein the process chamber area comprises a length and a width transverse to the length, and further wherein the length is greater than the width. The sample processing device also includes a valve chamber located within the process chamber area, wherein the valve chamber is isolated from the process chamber by a valve septum located between the valve chamber and the process chamber; and a detection window located within the process chamber area, wherein the detection window is transmissive for selected electromagnetic energy. The method also includes providing sample material in the process chamber; detecting a characteristic of the sample material in the process chamber through the detection window; forming an opening in the valve septum at a selected location within the process chamber area, wherein the selected location is correlated to the detected characteristic of the sample material; and moving only a portion of the sample material from the process chamber into the valve chamber through the opening formed in the valve septum by rotating the sample processing device.

These and other features and advantages of the present invention are described below in connection with various illustrative embodiments of the devices and methods of the present invention.

DETAILED DESCRIPTION OF ILLUSTRATIVE EMBODIMENTS OF THE INVENTION

Figure 1:
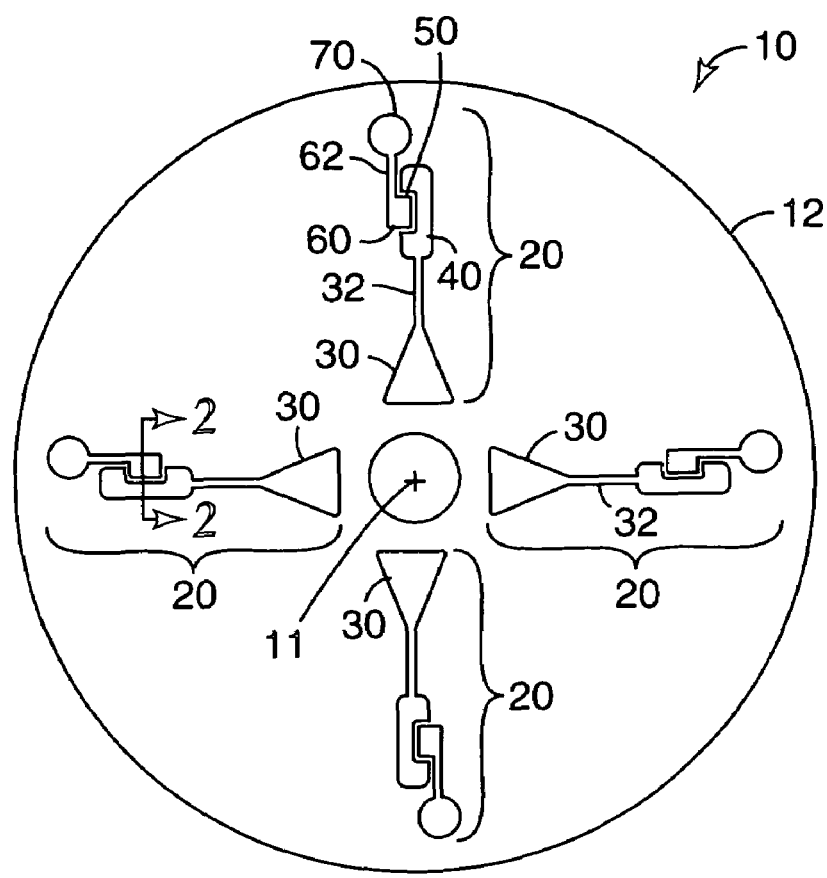
FIG. 1 is a plan view of one exemplary sample processing device according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. More particularly, the present invention provides sample processing devices that include one or more process arrays, each of which may preferably include a loading chamber, at least one process chamber, a valve chamber, and conduits for moving fluids between various components of the process arrays.

Although various constructions of illustrative embodiments are described below, sample processing devices of the present invention may be similar to those described in, e.g., U.S. Patent Application Publication Nos. US 2002/0064885 A1 (Bedingham et al.); US 2002/0048533 A1 (Harms et al.); US 2002/0047003 A1 (Bedingham et al.); and US 2003/0138779 A1 (Parthasarathy et al.); as well as U.S. Pat. No. 6,627,159 B1 (Bedingham et al.). The documents identified above all disclose a variety of different constructions of sample processing devices that could be used to manufacture sample processing devices according to the principles of the present invention.

Figure 2:
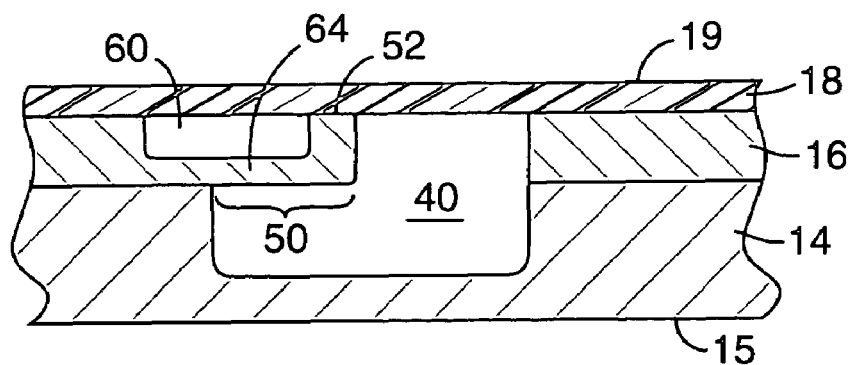
FIG. 2 is an enlarged cross-sectional view of a portion of the sample processing device of FIG. 1, taken along line 2-2 in FIG. 1.

One illustrative sample processing device manufactured according to the principles of the present invention is illustrated in FIGS. 1 & 2, where FIG. 1 is a plan view of one sample processing device 10 and FIG. 2 is an enlarged cross-sectional view of a portion of the sample processing device 10 (taken along line 2-2 in FIG. 1). The sample processing device 10 may preferably be in the shape of a circular disc as illustrated in FIG. 1, although any other shape that can be rotated could be used in place of a circular disc.

The sample processing device 10 includes at least one, and preferably multiple process arrays 20. If the sample processing device 10 is circular as depicted, it may be preferred that each of the depicted process arrays 20 extends from proximate a center 12 of the sample processing device 10 towards the periphery of the sample processing device 10. The process arrays 20 are depicted as being substantially aligned radially with respect to the center 12 of the sample processing device 10. Although this arrangement may be preferred, it will be understood that any arrangement of process arrays 20 may alternatively be used. Also, although the illustrated sample processing device 10 includes four process arrays 20, the exact number of process arrays provided in connection with a sample processing device manufactured according to the present invention may be greater than or less than four.

Each of the process arrays 20 (in the depicted embodiment) includes a loading chamber 30 connected to a process chamber 40 along a conduit 32. The process arrays 20 also include a valve chamber 60 connected to a second process chamber 70 by a conduit 62. The valve chamber 60 may preferably be located within a valve lip 50 extending into the area occupied by the process chamber 40 on the sample processing device 10.

It should be understood that a number of the features associated with one or more of the process arrays 20 may be optional. For example, the loading chambers 30 and associated conduits 32 may be optional where sample material can be introduced directly into the process chambers 40 through a different loading structure. At the same time, additional features may be provided with one or more of the process arrays 20. For example, two or more valve chambers 60 may be associated with one or more of the process arrays 20. Additional valve chambers may be associated with additional process chambers or other features.

Any loading structure provided in connection with the process arrays 20 may be designed to mate with an external apparatus (e.g., a pipette, hollow syringe, or other fluid delivery apparatus) to receive the sample material. The loading structure itself may define a volume (as, e.g., does loading chamber 30 of FIG. 1) or the loading structure may define no specific volume, but, instead, be a location at which sample material is to be introduced. For example, the loading structure may be provided in the form of a port through which a pipette or needle is to be inserted. In one embodiment, the loading structure may be, e.g., a designated location along a conduit that is adapted to receive a pipette, syringe needle, etc. The loading may be performed manually or by an automated system (e.g., robotic, etc.). Further, the sample processing device 10 may be loaded directly from another device (using an automated system or manually).

FIG. 2 is an enlarged cross-sectional view of the processing device 10 taken along line 2-2 in FIG. 1. Although sample processing devices of the present invention may be manufactured using any number of suitable construction techniques, one illustrative construction can be seen in the cross-sectional view of FIG. 2. The sample processing device 10 includes a base layer 14 attached to a valve layer 16. A cover layer 18 is attached to the valve layer 16 over the side of the valve layer 16 that faces away from the base layer 14.

The layers of sample processing device 10 may be manufactured of any suitable material or combination of materials. Examples of some suitable materials for the base layer 14 and/or valve layer 16 include, but are not limited to, polymeric material, glass, silicon, quartz, ceramics, etc. For those sample processing devices 10 in which the layers will be in direct contact with the sample materials, it may be preferred that the material or materials used for the layers be non-reactive with the sample materials. Examples of some suitable polymeric materials that could be used for the substrate in many different bioanalytical applications may include, but are not limited to, polycarbonate, polypropylene (e.g., isotactic polypropylene), polyethylene, polyester, etc.

The layers making up sample processing device 10 may be attached to each other by any suitable technique or combination of techniques. Suitable attachment techniques preferably have sufficient integrity such that the attachment can withstand the forces experienced during processing of sample materials in the process chambers. Examples of some of the suitable attachment techniques may include, e.g., adhesive attachment (using pressure sensitive adhesives, curable adhesives, hot melt adhesives, etc.), heat sealing, thermal welding, ultrasonic welding, chemical welding, solvent bonding, coextrusion, extrusion casting, etc. and combinations thereof. Furthermore, the techniques used to attach the different layers may be the same or different. For example, the technique or techniques used to attach the base layer 14 and the valve layer 16 may be the same or different as the technique or techniques used to attach the cover layer 18 and the valve layer 16.

FIG. 2 depicts a process chamber 40 in its cross-sectional view. Also seen in FIG. 2 is the valve lip 50 that, in the depicted embodiment is located within the area occupied by the process chamber, i.e., the process chamber area. The process chamber are may preferably be defined by projecting the process chamber boundaries onto either of the major sides of the sample processing device 10. In the embodiment depicted in FIG. 2, a first major side 15 of the sample processing device 10 is defined by the lowermost surface of base layer 14 (i.e., the surface facing away from valve layer 16) and a second major side 19 is defined by the uppermost surface of cover layer 18 (i.e., the surface facing away from the valve layer 16). It should be understood that "upper" and "lower" as used herein are with reference to FIG. 2 only and are not to be construed as limiting the orientation of the sample processing device 10 in use.

The valve lip 50 is depicted as extending into the process chamber area as defined by the outermost boundaries of process chamber 40. Because the valve lip 50 is located within the process chamber area, the valve lip 50 may be described as overhanging a portion of the process chamber 40 or being cantilevered over a portion of the process chamber 40.

Preferred process chambers of the present invention may include a detection window that allows the detection of one or more characteristics of any sample material in the process chamber 40. It may be preferred that the detection be achieved using selected light, where the term "light" refers to electromagnetic energy, whether visible to the human eye or not. It may be preferred that the light fall within a range of ultraviolet to infrared electromagnetic energy, and, in some instances, it may be preferred that light include electromagnetic energy in the spectrum visible to the human eye. Furthermore, the selected light may be, e.g., light of one or more particular wavelengths, one or more ranges of wavelengths, one or more polarization states, or combinations thereof.

In the embodiment depicted in FIG. 2, the detection window may be provided in the cover layer 18 or in the base layer 14 (or both). Regardless of which component is used as the detection window, the materials used preferably transmit significant portions of selected light. For the purposes of the present invention, significant portions may be, e.g., 50% or more of normal incident selected light, more preferably 75% or more of normal incident selected light. Examples of some suitable materials for the detection window include, but are not limited to, e.g., polypropylenes, polyesters, polycarbonates, polyethylenes, polypropylene-polyethylene copolymers, cyclo-olefin polymers (e.g., polydicyclopentadiene), etc.

In some instances, it may be preferred that the base layer 14 and/or the cover layer 18 of the sample processing device 10 be opaque such that the sample processing device 10 is opaque between the volume of the process chamber volume 14 and at least one side of the sample processing device 10. By opaque, it is meant that transmission of the selected light as described above is substantially prevented (e.g., 5% or less of such normally incident light is transmitted).

Valve chamber 60 is depicted in FIG. 2 and may preferably be at least partially located within the valve lip 50 as seen in FIG. 2. At least a portion of the valve chamber 60 may preferably be located between the second major side 19 of the sample processing device 10 and at least a portion of the process chamber 40. The valve chamber 60 is also preferably isolated from the process chamber 40 by a valve septum 64 separating the valve chamber 64 and the process chamber 40, such that a portion of the volume of the process chamber 40 lies between the valve septum 64 and the first major side 15 of the sample processing device 10. In the depicted embodiment, the cover layer 18 is preferably sealed to the valve lip 50 along surface 52 to isolate the valve chamber 60 from the process chamber 50.

The valve septum 64 is preferably formed of material in which openings can be formed by non-contact methods, e.g., laser ablation, etc. The energy used to form openings in the valve septum 64 can be directed onto the valve septum 64 either through the cover layer 18 or through the base layer 14 (or through both). It may be preferred, however, that the energy be directed at the valve septum 64 through the cover layer 18 to avoid issues that may be associated with directing the energy through the sample material in the process chamber 40 before it reaches the valve septum 64.

One illustrative method of using a process array 120 will now be described with respect to FIGS. 3A-3D, each of which is a plan view of the process array in various stages of one illustrative method according to the present invention. The process array 120 depicted in each of the figures includes a loading chamber 130 connected to a process chamber 140 through conduit 132. The process array also includes a valve lip 150 and a valve chamber 160 located within a portion of the valve lip 150. The valve lip 150 and the valve chamber 160 define a valve septum 164 separating and isolating the valve chamber 160 from the process chamber 140 before any openings are formed through the valve septum 164. The valve septum 164 boundary is depicted as a broken line in the figures because it may not be visible to the naked eye.

Another feature of the process array 120 is a detection window 142 through selected light can be transmitted into and/or out of the process chamber 140. The detection window 142 may be formed through either major side of the device in which process array 120 is located (or through both major sides if so desired). In the depicted embodiment, the detection window 142 may preferably be defined by that portion of the area occupied by the process chamber 140 that is not also occupied by the valve lip 150. In another manner of characterizing the detection window 142, the detection window 142 and the valve lip 150 (and/or valve chamber 160 contained therein) may be described as occupying mutually exclusive portions of the area of the process chamber 140.

The process array 120 also includes an output process chamber 170 connected to the valve chamber 160 through conduit 162. The output process chamber 170 may include, e.g., one or more reagents 172 located therein. The reagent 172 may be fixed within the process chamber 170 or it may be loose within the process chamber. Although depicted in process chamber 170, one or more reagents may be provided at any suitable location or locations within the process array 120, e.g., the loading chamber 130, conduits 132 & 162, process chamber 140, valve chamber 160, etc.

The use of reagents is optional, i.e., sample processing devices of the present invention may or may not include any reagents in the process chambers. In another variation, some of the process chambers in different process arrays may include a reagent, while others do not. In yet another variation, different process chambers may contain different reagents. Further, the interior of the process chamber structures may be coated or otherwise processed to control the adhesion of reagents.

The process chamber 140 (and its associated process chamber area) may preferably have a length (measured along, e.g., axis 121 in FIG. 3A) that is greater than the width of the process chamber 140, where the process chamber width is measured perpendicular to the process chamber length. As such, the process chamber 140 may be described as "elongated." It may be preferred that the axis 121 along which the process chamber 140 is elongated be aligned with a radial direction extending from an axis of rotation about which the sample processing device containing process array is rotated (if rotation is the driving force used to effect fluid transfer).

In other aspects, it may be preferred that the detection window 142 be at least coextensive along the length of the process chamber 140 with the valve septum 164. Although the depicted detection window 142 is a single unitary feature, it will be understood that more two or more detection windows could be provided for each process chamber 140. For example, a plurality of independent detection windows could be distributed along the length of the process chamber 140 (e.g., alongside the valve septum 164.

Another manner of characterizing the relative sizes of the various features may be, e.g., that the valve septum 164 extends along the length of the process chamber area for 30% or more (or, alternatively, for 50% or more) of a maximum length of the process chamber 140 (along its elongation axis 121). Such a characterization of the dimensions of valve septum 164 may be expressed in actual measurements for many sample processing devices, e.g., the valve septum 164 may be described as extending for a length of 1 millimeter or more along the length of the process chamber 140.

Figure 3A:
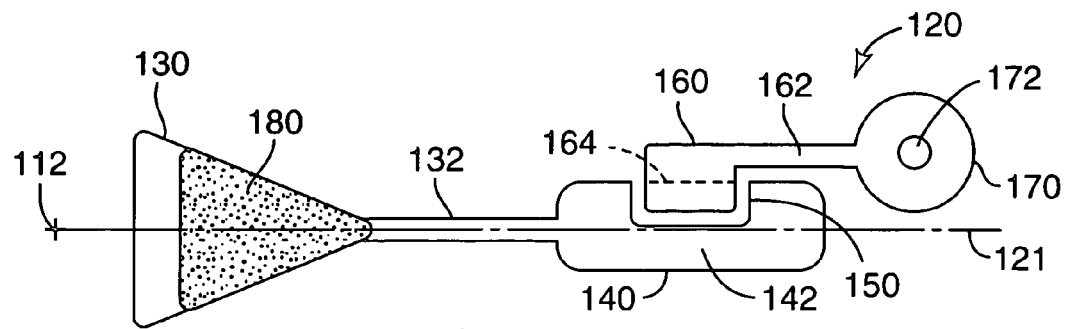
FIGS. 3A-3D depict one exemplary method of moving fluid through a process array including a process chamber and a valve chamber.

The first stage of the depicted method is seen in FIG. 3A, where the loading chamber 130 includes sample material 180 located therein. For the purposes of the illustrated method, the sample material 180 is whole blood. After loading, the blood 180 is preferably transferred to the process chamber 140 through conduit 132. The transfer may preferably be effected by rotating the process array 120 about an axis of rotation 111. The rotation may preferably occur, for example, in the plane of the paper on which FIG. 3A is located, although any rotation about point 111 in which process chamber 140 is moved in an arc about a point located on the opposite side of the loading chamber 130 from the process chamber 140 may be acceptable.

The process arrays used in sample processing devices of the present invention may preferably be "unvented." As used in connection with the present invention, an "unvented process array" is a process array (i.e., at least two connected chambers) in which the only openings leading into the process array are located in the loading structure, e.g., the loading chamber. In other words, to reach the process chamber within an unvented process array, sample materials must be delivered to the loading chamber. Similarly, any air or other fluid located within the process array before loading of the sample material must also escape from the process array through the loading chamber. In contrast, a vented process array would include at least one opening outside of the loading chamber. That opening would allow for the escape of any air or other fluid located within the process array before loading.

Moving sample material through sample processing devices that include unvented process arrays may be facilitated by alternately accelerating and decelerating the device during rotation, essentially burping the sample materials through the conduits and process chambers. The rotating may be performed using at least two acceleration/deceleration cycles, i.e., an initial acceleration, followed by deceleration, second round of acceleration, and second round of deceleration. It may further be helpful if the acceleration and/or deceleration are rapid. The rotation may also preferably only be in one direction, i.e., it may not be necessary to reverse the direction of rotation during the loading process. Such a loading process allows sample materials to displace the air in those portions of the process arrays that are located farther from the center of rotation of the device. The actual acceleration and deceleration rates may vary based on a variety of factors such as temperature, size of the device, distance of the sample material from the axis of rotation, materials used to manufacture the devices, properties of the sample materials (e.g., viscosity), etc.

Figure 3B:
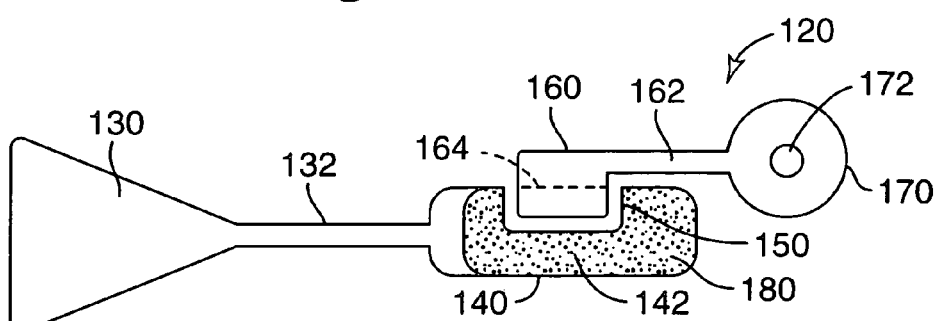

FIG. 3B depicts the process array after movement of the blood 180 into the process chamber 140. The blood 180 remains in the process chamber 140, i.e., does not travel into the valve chamber 160, because the valve chamber 160 is isolated from the process chamber 140 by the valve septum 164.

Figure 3C:
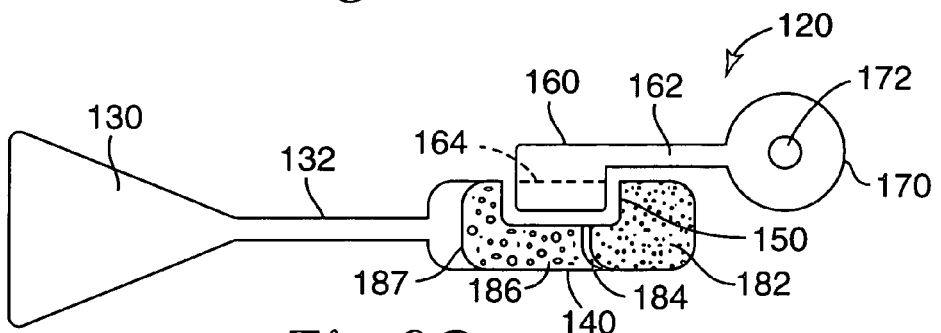
Figure 3D:
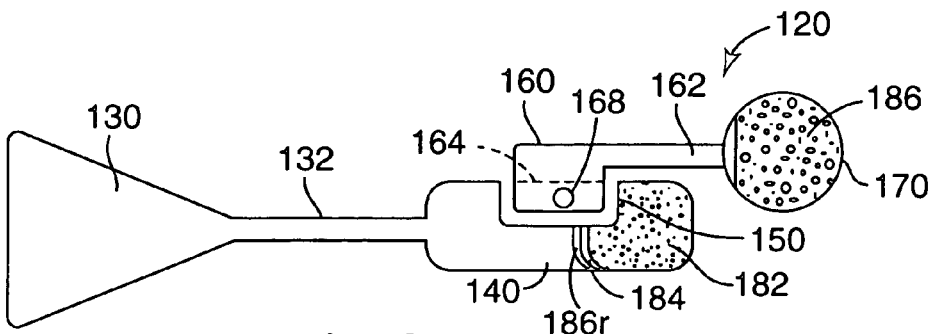

Additional rotation of the process array 120 may preferably result in separation of the components of the blood 180 into, as seen in FIG. 3C, red blood cells 182, a buffy coat layer 184, and plasma 186. The separation is typically a result of centrifugal forces and the relative densities of the materials.

If the precise volume of the different components in each sample of blood 180 (or if the volume of the blood sample 180 itself) is not known, the location of the boundaries between the different separated layers may not be known. In connection with the present invention, however, it may preferably be possible to detect the locations of the boundaries between the different separated components.

Such detection may preferably occur through the detection window using any suitable selected light. The light may be transmitted through or reflected from the blood components 182, 184 & 186 to obtain an image of the sample material in the process chamber 140. In another alternative, absorbance of light may be used to detect the boundaries or locations of one or more selected components. It may be preferable to determine the location of all features or characteristics of the sample material, i.e., the location of all boundaries, including the free surface 187 of the plasma 186. In other instances, it may be sufficient to determine the location of only one feature, e.g., the boundary between the buffy coat layer 184 and the plasma 186, where the detected characteristic provides sufficient information to perform the next step in the method.

After the suitable characteristic or characteristics of the materials in the process chamber 140 have been detected, an opening 168 is preferably formed in the valve septum 164 at the desired location. In the depicted method, the desired location for opening 168 is chosen to remove a portion of the plasma 186 from the process chamber 140. It may be desirable that substantially all of the plasma 186 be removed, leaving only a small amount (see 186*r* in FIG. 3D) in the process chamber 140. It may be necessary to leave a small amount of plasma in the process chamber 140 to limit or prevent the transfer of red blood cells 182 out of the process chamber 140.

The opening 168 can be formed by any suitable non-contact technique. One such technique may be, e.g., laser ablation of the valve septum 168. Other techniques may include, but are not limited to, e.g., focused optical heating, etc.

After the opening 168 is formed, additional rotation of the process array 120 preferably moves the plasma 186 from the process chamber 140 into the valve chamber 160 through opening 168, followed by transfer into the output process chamber 170 through conduit 162. As a result, the plasma 186 is located in the process chamber 170, with a small remainder of plasma 186*r* in the process chamber 140 along with the buffy coat layer 184 and red blood cells 182.

Figure 4:
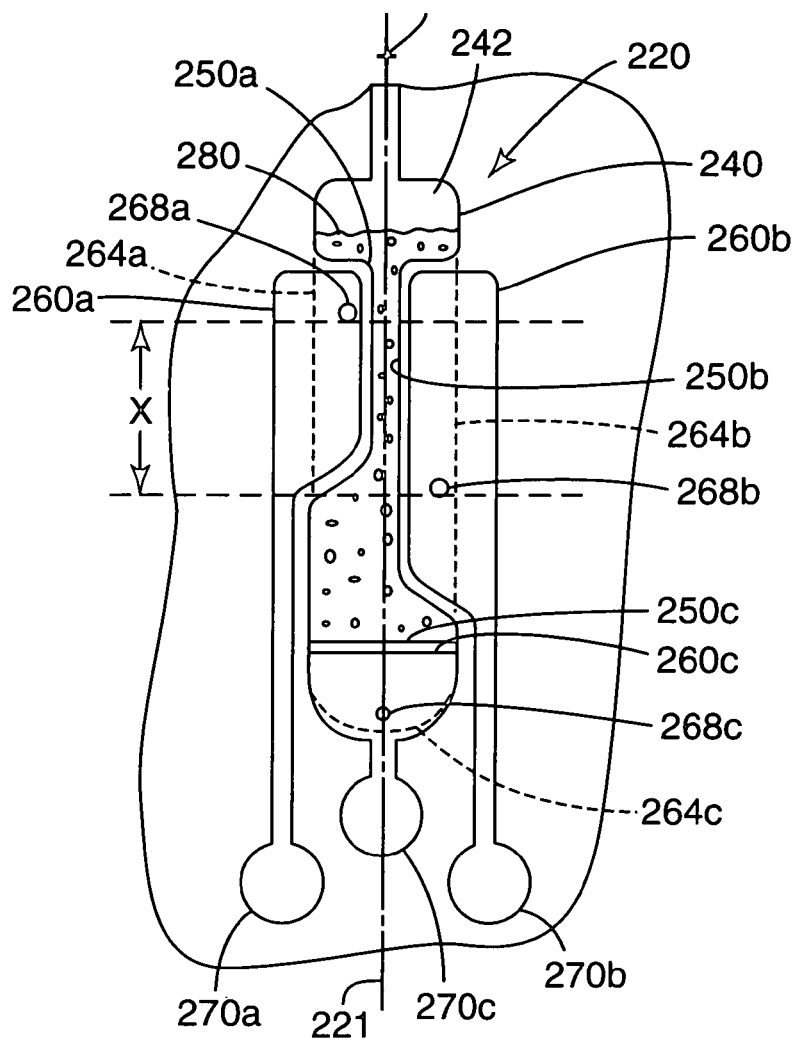
FIG. 4 is a plan view of an alternative process chamber and multiple valve chambers in accordance with the present invention.

A portion of another embodiment of a process array 220 including a process chamber 240 and valve structures according to the present invention is depicted in FIG. 4. In the depicted embodiment, the process chamber 240 is elongated along axis 221 and the process array 220 is designed for rotation to provide the force to move fluids. The rotation may be about point 211 which, in the depicted embodiment, lies on axis 221. It should, however, be understood that the point about which the process array is rotated is not required to lie on axis 221.

The process chamber 240 is shown in broken lines where the valve lips 250*a*, 250*b* and 250*c* extend into the process chamber area and in solid lines where the valve lips 250*a*, 250*b* and 250*c* do not extend into the process chamber area. It may be preferred that in those portions of the process chamber area that are not occupied by the valve lips 250*a*, 250*b* and 250*c*, the process chamber 240 include a detection window 242 that allows for the transmission of selected light into and/or out of the process chamber 240 to allow for detection of sample material 280 in the process chamber 240.

The process array 220 also includes valve chambers 260*a*, 260*b*, and 260*c* isolated and separated from the process chamber 240. The valve chambers 260*a*, 260*b*, and 260*c* are each in communication with a chamber 270*a*, 270*b*, and 270*c* (respectively). The valve chambers 260*a*, 260*b*, and 260*c* may be connected to their respective chambers 270*a*, 270*b*, and 270*c* by a conduit as shown in FIG. 4.

Each of the valve chambers 260*a*, 260*b*, and 260*c* may preferably be located, at least in part, on a valve lip 250*a*, 250*b* and 250*c* (respectively). Each of the valve chambers 260*a*, 260*b*, and 260*c* may also preferably be isolated and separated from the process chamber 240 by a valve septum 264*a*, 264*b*, and 264*c* located within each of the valve chambers 260*a*, 260*b*, and 260*c*. Each of the valve septums 264*a*, 264*b*, and 264*c* is defined, in part, by the broken lines of process chamber 240.

The multiple valve chambers 260*a*, 260*b*, and 260*c* provided in connection with the process chamber 240 may provide the ability to selectively remove different portions of any sample material in the process chamber and to move that sample material to different chambers 270*a*, 270*b*, and 270*c*. For example, a first portion of sample material 280 in the process chamber 240 may be moved into chamber 270*a* by forming an opening 268*a* in valve septum 264*a* of valve chamber 260*a*.

After moving the first portion of sample material 280 into chamber 270*a* through opening 268*a* in valve chamber 260*a*, another opening 268*b* may be provided in valve septum 264*b* of valve chamber 260*b* to move a second portion of the sample material 280 into chamber 270*b*. The second portion will typically include the sample material 280 located between openings 268*a* and 268*b*. The distance separating those two openings along the length of the process chamber 240 is indicated by x in FIG. 4. As a result, the volume of the second portion of sample material 280 can be determined if the cross-sectional area of the process chamber 240 (taken in a plane perpendicular to the axis 221) is known. As a result, it may be possible to move a known or selected volume of sample material into chamber 270*b* by forming openings 268*a* and 268*b* a selected distance apart from each other.

The process chamber 240 also includes a third valve chamber 260*c* located in a valve lip 250*c* at the end of the process chamber 240 farthest from the point 211 about which the process array 220 may be rotated. The valve lip 250*c* extends over the entire width of the process chamber 240 (in contrast to the valve lips 250*a* and 250*b* that extend over only a portion of the width of the process chamber 240).

Figure 5:
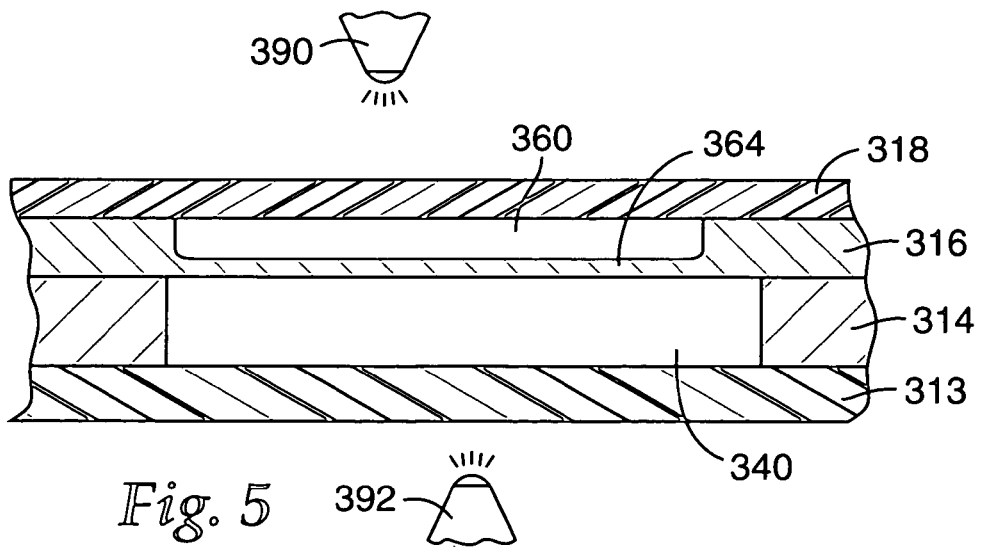
FIG. 5 is a cross-sectional view of another alternative process chamber and valve chamber construction according to the present invention, including optional detection apparatus facing both major sides of the sample processing device.

FIG. 5 depicts another process chamber 340 in connection with the present invention in cross-section. The process chamber 340 is formed in a sample processing device 310 that includes a base layer 313, intermediate layer 314, valve layer 316 and cover layer 318. The various layers may be attached to each other by any suitable combination of techniques.

Although the layers are depicted as single, homogeneous constructions, it will be understood that one or more of the layers could be formed of multiple materials and/or layers. Furthermore, it may be possible to combine some of the layers. For example, layers 313 and 314 may be combined (as an example, see layer 14 in the cross-sectional view of FIG. 2). Alternatively, it may be possible to combine layers 314 and 316 into a single structure that could be formed by, e.g., molding, extrusion, etc.

The construction seen in FIG. 5 includes a valve chamber 360 separated from the process chamber 340 by a valve septum 364. The valve chamber 360 is further defined by the cover layer 318. A device 390 is also depicted in FIG. 5 that can be used to, e.g., form an opening in the valve septum 364. The device 390 may be, e.g., a laser, etc. that can preferably deliver the energy necessary to form an opening in the valve septum 364 without forming an opening in the cover layer 318.

If the energy required to form openings in the valve septum 364 can be directed through the cover layer 318, then the base layer 313 may be formed of any material that may block such energy. For example, the base layer 313 may be made of, e.g., a metallic foil or other material. If the valve layer 316 and/or valve septum 364 allow for the passage of sufficient amounts of selected wavelengths of light, it may be possible to detect sample material in the process chamber 340 through the valve layer 316 and/or valve septum 364.

If, alternatively, the valve layer 316 and valve septum 364 block the passage of light such that detection of sample material in the process chamber 340 cannot be performed, then it may be desirable to detect sample material in the process chamber 340 through the base layer 313. Such detection may be accomplished using detection device 392 as seen in FIG. 5 that can detect sample material in the process chamber 340 through the layer 313. In some instances, it may be possible to form openings in the valve septum 364 using device 392 directing energy through layer 313 (if the passage of such energy through sample material in the process chamber 340 is acceptable).

As used herein and in the appended claims, the singular forms "a," "and," and "the" include plural referents unless the context clearly dictates otherwise. Thus, for example, reference to "a valve lip" includes a plurality of valve lips and reference to "the process chamber" includes reference to one or more process chambers and equivalents thereof known to those skilled in the art.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A valved process chamber on a sample processing device, the valved process chamber comprising:

a process chamber comprising a process chamber volume located between opposing first and second major sides of the sample processing device, wherein the process chamber occupies a process chamber area on the sample processing device, and wherein the process chamber area comprises a length and a width transverse to the length, and further wherein the length is greater than the width;

a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and the first major side of the sample processing device;

wherein at least a portion of the valve chamber is located within a valve lip extending into the process chamber area, and wherein the valve septum is formed in the valve lip; and a detection window located within the process chamber area, wherein the detection window is transmissive to selected electromagnetic energy directed into and/or out of the process chamber volume.

2. A valved process chamber according to claim 1, wherein the detection window is coextensive along the length of the process chamber with the valve septum.

3. A valved process chamber according to claim 1, wherein the detection window is formed through the first major side of the sample processing device.

4. A valved process chamber according to claim 1, wherein the detection window is formed through the second major side of the sample processing device.

5. A valved process chamber according to claim 1, wherein the valve chamber and the detection window occupy mutually exclusive portions of the process chamber area.

6. A valved process chamber according to claim 1, wherein the detection window is formed through the second major side of the sample processing device, and wherein the valve chamber and the detection window occupy mutually exclusive portions of the process chamber area.

7. A valved process chamber according to claim 1, wherein the valve septum extends along the length of the process chamber area for 30% or more of a maximum length of the process chamber area.

8. A valved process chamber according to claim 1, wherein the valve septum extends for a length of 1 millimeter or more along the length of the process chamber.

9. A valved process chamber according to claim 1, wherein the sample processing device is opaque between the process chamber volume and the first major side of the sample processing device.

10. A valved process chamber according to claim 1, wherein the valve lip occupies only a portion of the width of the process chamber area.

11. A valved process chamber according to claim 10, wherein the detection window occupies at least a portion of the width of the process chamber area that is not occupied by the valve lip.

12. A valved process chamber on a sample processing device, the valved process chamber comprising:

a process chamber comprising a process chamber volume located between opposing first and second major sides of the sample processing device, wherein the process chamber occupies a process chamber area on the sample processing device, and wherein the process chamber area comprises a length and a width transverse to the length, and further wherein the length is greater than the width;
a detection window located within the process chamber area, wherein the detection window is transmissive to selected electromagnetic energy directed into and/or out of the process chamber volume; and
a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device, and further wherein the valve chamber and the detection window occupy mutually exclusive portions of the process chamber area, and still further wherein at least a portion of the valve chamber is located within a valve lip extending into the process chamber area, and wherein the valve septum is formed in the valve lip.

13. A method of selectively removing sample material from a process chamber, the method comprising:
providing a sample processing device comprising:
a process chamber comprising a process chamber volume, wherein the process chamber occupies a process chamber area on the sample processing device, and wherein the process chamber area comprises a length and a width transverse to the length, and further wherein the length is greater than the width;
a valve chamber located within the process chamber are; wherein the valve chamber is isolated from the process chamber by a valve septum located between the valve chamber and the process chamber; and
a detection window located within the process chamber area, wherein the detection window is transmissive for selected electromagnetic energy;
providing sample material in the process chamber;
detecting a characteristic of the sample material in the process chamber through the detection window;
forming an opening in the valve septum at a selected location along the length of the process chamber, wherein the selected location is correlated to the detected characteristic of the sample material; and
moving only a portion of the sample material from the process chamber into the valve chamber through the opening formed in the valve septum.

14. A method according to claim 13, wherein moving only a portion of the sample material from the process chamber into the valve chamber comprises rotating the sample processing device.

15. A method according to claim 13, wherein the process chamber area comprises a length and a width transverse to the length, and further wherein the length is greater than the width.

16. A method according to claim 13, wherein the detected characteristic comprises a free surface of the sample material, and wherein the portion of the sample material moved from the process chamber into the valve chamber comprises a selected volume of the sample material.

17. A method according to claim 13, further comprising rotating the sample processing device to separate components of the sample material in the process chamber.

18. A method according to claim 17, wherein the detected characteristic of the sample material comprises a boundary between the separated components of the sample material, and wherein the portion of the sample material moved from the process chamber into the valve chamber comprises a portion of a selected component of the sample material.

19. A method according to claim 13, wherein moving only a portion of the sample material from the process chamber into the valve chamber comprises moving a selected volume of the sample material from the process chamber into the valve chamber.

20. A method according to claim 13, wherein the sample material comprises blood.

21. A method of selectively removing sample material from a process chamber, the method comprising:
providing a sample processing device comprising:
a process chamber comprising a process chamber volume, wherein the process chamber occupies a process chamber area on the sample processing device, and wherein the process chamber area comprises a length and a width transverse to the length, and further wherein the length is greater than the width;
a valve chamber located within the process chamber area, wherein the valve chamber is isolated from the process chamber by a valve septum located between the valve chamber and the process chamber; and
a detection window located within the process chamber area, wherein the detection window is transmissive for selected electromagnetic energy;
providing sample material in the process chamber;
detecting a characteristic of the sample material in the process chamber through the detection window;
forming an opening in the valve septum at a selected location within the process chamber area, wherein the selected location is correlated to the detected characteristic of the sample material; and
moving only a portion of the sample material from the process chamber into the valve chamber through the opening formed in the valve septum by rotating the sample processing device.

22. A sample processing device comprising a plurality of process arrays, wherein each process array of the plurality of process arrays comprises:
a first process chamber that comprises a process chamber volume located between opposing first and second major sides of the sample processing device, wherein the first process chamber occupies a first process chamber area on the sample processing device, and wherein the first process chamber area comprises a length and a width transverse to the length, and further wherein the length is greater than the width;
a valve chamber located within the first process chamber area, the valve chamber located between the first process chamber volume and the second major side of the sample processing device, wherein the valve chamber is isolated from the first process chamber by a valve septum separating the valve chamber and the first process chamber, and wherein a portion of the first process chamber volume lies between the valve septum and the first major side of the sample processing device;
a detection window located within the first process chamber area, wherein the detection window is transmissive to selected electromagnetic energy directed into and/or out of the first process chamber volume;
a conduit in fluid communication with the valve chamber; and
a second process chamber in fluid communication with the valve chamber through the conduit; wherein an opening formed in the valve septum places the second process chamber in fluid communication with the first process chamber.

23. A sample processing device according to claim 22, wherein each process array of the plurality of process arrays comprises a loading chamber in fluid communication with first process chamber.

24. A sample processing device according to claim 22, wherein each process array of the plurality of process arrays comprises a loading chamber in fluid communication with first process chamber through a conduit.

25. A sample processing device according to claim 22, wherein each process array of the plurality of process arrays extends from proximate a center of the sample processing device towards a periphery of the sample processing device such that the first process chamber is located closer to the center than the second process chamber for each process array of the plurality of process arrays.

26. A sample processing device according to claim 22, wherein, for each process array of the plurality of process arrays, at least a portion of the valve chamber is located within a valve lip extending into the first process chamber area, and wherein the valve septum is formed in the valve lip.

27. A sample processing device according to claim 26, wherein the valve lip occupies only a portion of the width of the first process chamber area.

28. A sample processing device according to claim 27, wherein, for each process array of the plurality of process arrays, the detection window occupies at least a portion of the width of the first process chamber area that is not occupied by the valve lip.

29. A sample processing device according to claim 22, wherein, for each process array of the plurality of process arrays, the valve chamber and the detection window occupy mutually exclusive portions of the first process chamber area.

* * * * *

UNITED STATES PATENT AND TRADEMARK OFFICE
CERTIFICATE OF CORRECTION

PATENT NO. : 7,322,254 B2
APPLICATION NO. : 10/734717
DATED : January 29, 2008
INVENTOR(S) : William Bedingham It is certified that error appears in the above-identified patent and that said Letters Patent is hereby corrected as shown below:

<u>On Sheet 3 of 3 of the Drawings, under (FIG.4)</u>
Line 1, (Above Reference Numeral "242"), insert -- 211 --.

<u>Column 13</u>
Line 34, in Claim 13, delete "are;" and insert -- area, --, therefor.

Signed and Sealed this

Second Day of September, 2008

JON W. DUDAS
*Director of the United States Patent and Trademark Office*